United States Patent [19]
Baranski et al.

[11] Patent Number: 6,117,826
[45] Date of Patent: Sep. 12, 2000

[54] DITHIOCARBAMYL DERIVATIVES USEFUL AS LUBRICANT ADDITIVES

[75] Inventors: John Robert Baranski, Southington, Conn.; Cyril Andrew Migdal, Pleasant Valley, N.Y.

[73] Assignee: Uniroyal Chemical Company, Inc., Middlebury, Conn.

[21] Appl. No.: 09/149,641

[22] Filed: Sep. 8, 1998

[51] Int. Cl.[7] ..................... C10M 135/18; C10M 139/00
[52] U.S. Cl. ........................ 508/363; 508/555; 508/562; 556/63; 560/148
[58] Field of Search ................... 508/363, 555, 508/562; 556/63; 560/148

[56] References Cited

U.S. PATENT DOCUMENTS

| | | | |
|---|---|---|---|
| 3,356,702 | 12/1967 | Farmer | 260/429 |
| 4,098,705 | 7/1978 | Sakurai | 252/33.6 |
| 4,178,258 | 12/1979 | Papay | 252/32.7 |
| 5,686,397 | 11/1997 | Baranski | 508/274 |
| 5,789,357 | 8/1998 | Baranski et al. | 508/513 |
| 5,872,286 | 2/1999 | Baranski et al. | 508/444 |

OTHER PUBLICATIONS

Chemical Abstracts 122670 : 1987.

*Primary Examiner*—Jacqueline V. Howard
*Attorney, Agent, or Firm*—Daniel Reitenbach

[57] ABSTRACT

Dithiocarbamyl derivatives, useful as multifunctional additives for lubricating oils, of the formula

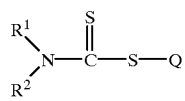

(I)

wherein

Q is

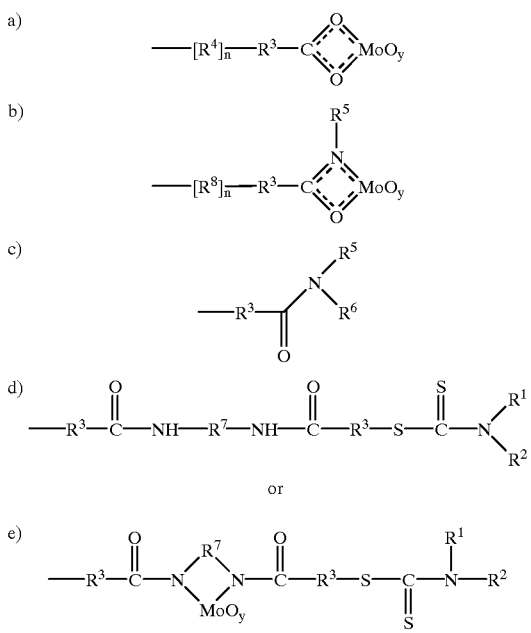

$R^1$ and $R^2$ are each independently $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^3$ is $C_1$–$C_{20}$ alkylene; $R^4$ is —$R^3$—C(O)—O—; $R^5$ and $R^6$ are each independently hydrogen, $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^7$ is $C_1$–$C_{20}$ alkylene, optionally substituted with —$OR^5$ or —COOH; $R^8$ is —$R^3$—C(O)—$NR^5$—; n is 0, 1, 2 or 3; and y is 0, 1, 2, or 3.

20 Claims, No Drawings

DITHIOCARBAMYL DERIVATIVES USEFUL AS LUBRICANT ADDITIVES

FIELD OF THE INVENTION

This invention relates to dithiocarbamyl derivatives and their use as multifunctional additives for lubricating oils.

BACKGROUND OF THE INVENTION

Improving fuel economy is an important aspect of formulating a motor oil. It is known that the fuel efficiency of an engine oil can be improved by using friction reducing additives. It is known that these additives must be active at engine operational temperature in order to be most effective.

Zinc dialkyldithiophosphates (ZDDPs) have been used as anti-fatigue, anti-wear, extreme pressure and friction modifying additives for lubricating oils for many years. However, they are subject to several drawbacks owing to their zinc and phosphorus contents. During operation of an internal combustion engine, lubricating oil enters the combustion chambers by means such as clinging to cylinder walls as the piston makes its down stroke. When phosphorus-containing lubricating oil compositions enter the combustion reaction, phosphorus enters the exhaust stream where it acts as a catalyst poison thus shortening the useful life of the catalytic converter. In addition, the presence of zinc contributes to the emission of particulates in the exhaust.

In view of the aforementioned shortcomings with the known zinc and phosphorus-containing additives, efforts have been made to provide lubricating oil additives which contain neither zinc nor phosphorus. Illustrative of non-zinc (i.e., ashless), non-phosphorus-containing lubricating oil additives are the reaction products of 2,5-dimercapto-1,3,4-thiadiazole and unsaturated mono-, di- and tri-glycerides of U.S. Pat. No. 5,512,190 and the dialkyl dithiocarbamate-derived organic ethers of U.S. Pat. No. 5,514,189.

Certain molybdenum dithiocarbamates are known as useful as lubricant additives. For example, U.S. Pat. No. 3,356,702 describes certain molybdenum oxysulfate dithiocarbamates useful as extreme pressure agent, antioxidant and wear inhibitor for lubricants. U.S. Pat. No. 4,098,705 describes certain sulfur containing molybdenum dihydrocarbyldithiocarbamates useful as lubricant additives. U.S. Pat. No. 4,178,258 describes lubricating oil compositions comprising certain molybdenum bis(dialkyldithiocarbamates).

It a purpose of this invention to provide novel dithiocarbamyl carboxylic acid and amide compounds useful as lubricant additives. It is also a purpose of this invention to provide novel additives for lubricating oils that can improve the friction reducing properties of the oils.

SUMMARY OF THE INVENTION

This invention relates to a dithiocarbamyl compound of the formula

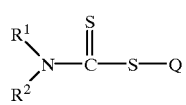

(I)

wherein

Q is

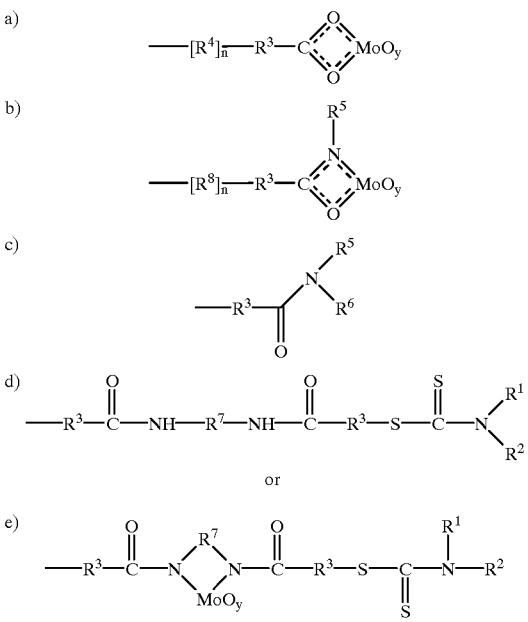

$R^1$ and $R^2$ are each independently $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^3$ is $C_1$–$C_{20}$ alkylene; $R^4$ is —$R^3$—C(O)—O—; $R^5$ and $R^6$ are each independently hydrogen, $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^7$ is $C_1$–$C_{20}$ alkylene, optionally substituted with —$OR^5$ or —COOH; $R^8$ is —$R^3$—C(O)—$NR^5$—; m and n are each, independently, 0, 1, 2 or 3; and y is 0, 1, 2, 3, or 4.

The dithiocarbamyl compounds of this invention are useful as ashless anti-wear, antioxidant, friction reducing, and extreme pressure additives for lubricating oils.

This invention also relates to a lubricating oil composition comprising a lubricating oil and a functional property-improving amount of at least one dithiocarbamyl compound of formula I.

This invention further relates to a method for improving at least one functional property of a lubricating oil which comprises adding to the lubricating oil a functional property-improving amount of at least one dithiocarbamyl compound of formula I.

DESCRIPTION OF THE INVENTION

The dithiocarbamyl compound of this invention can have the formula

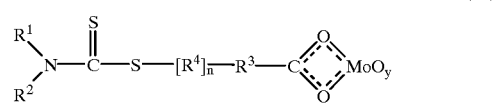

(IA)

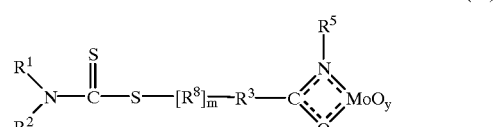

(IB)

-continued

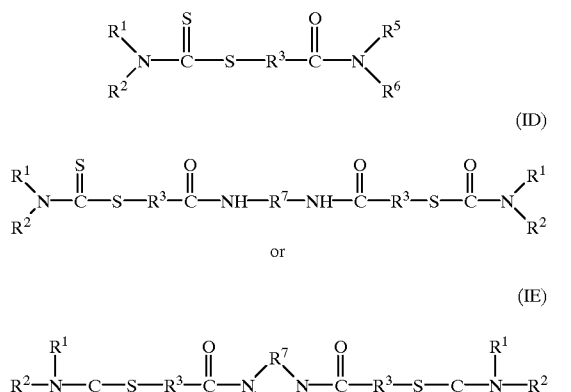

wherein $R^1$, $R^2$, $R^3$, $R^4$, $R^5$, $R^6$, $R^7$, $R^8$, m, n and y are as described above.

For the purposes of this invention, the formula

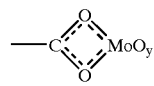

means a carboxylic acid oxomolybdenum complex.

For the purposes of this invention, the formula

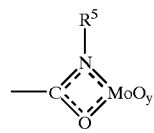

means an amide oxomolybdenum complex.

$R^1$ and $R^2$ are preferably, each independently a straight-chained, branched or cyclic alkyl group of from about 2 to about 30 carbon atoms, more preferably, an alkyl group of from about 4 to about 24 carbon atoms; $R^3$ is preferably, a divalent alkylene group of from about 2 to about 12 carbon atoms, more preferably, a divalent alkylene group of from 2 to about 6 carbon atoms; $R^5$ and $R^6$ are preferably, each independently, hydrogen, a straight-chained, branched or cyclic alkyl group of from about 2 to about 30 carbon atoms, more preferably, hydrogen or an alkyl group of from about 4 to about 24 carbon atoms; $R^7$ is preferably, a divalent alkylene group of from about 2 to about 12 carbon atoms, more preferably, a divalent alkylene group of from 2 to about 6 carbon atoms substituted with —$OR^5$ or —COOH; m and n are each preferably 1; and y is preferably 2.

The functional properties of a lubricant which can be improved by the use of the molybdenum dithiocarbamyl compounds of this invention, include the anti-wear, antioxidant, and friction reducing properties of the lubricant.

The molybdenum dithiocarbamyl carboxylic acid compounds of formula IA can be prepared in accordance with the following sequence of reaction steps in Procedure A below:

Procedure A:

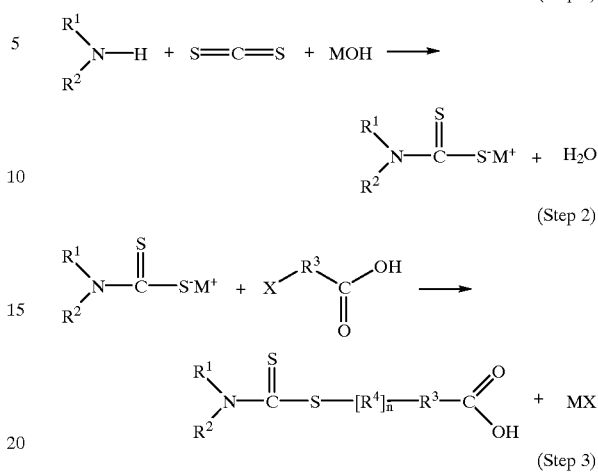

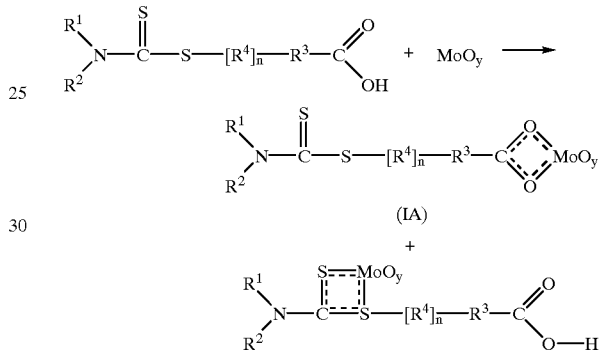

$R^1$, $R^2$, $R^3$, $R^4$, n and y are each as defined above, M is an alkali metal, such as sodium, and X is halogen, preferably chlorine.

In step 1 of Procedure A, the dihydrocarbylamine $R^1R^2NH$ is reacted with an equimolar amount of alkali metal hydroxide MOH and carbon disulfide, the latter preferably in slight molar excess, to provide an alkali metal di(hydrocarbyl)thiocarbamate intermediate $R^1R^2NCSSM$. Useful dihydrocarbylamines are those in which hydrocarbyl groups $R^1$ and $R^2$ are selected from among alkyl, cycloalkyl, alkaryl and aralkyl groups of up to about 60 carbon atoms. Preferred dihydrocarbylamine reactants are dialkylamines in which each alkyl group contains from about 2 to about 30, and more preferably from about 4 to about 24, carbon atoms. The alkali metal hydroxide can be, e.g., aqueous sodium hydroxide and the reaction can be advantageously conducted in a suitable solvent with water and/or a lower alkanol such as methanol, ethanol, propanol, 2-propanol, n-butanol, sec-butanol, t-butanol, or preferably, isopropanol.

In Step 2 of Procedure A, an equimolar amount of haloalkanoic acid, e.g., 3-chloropropionic acid, is added to the reaction medium of Step 1 where it reacts with alkali metal di(hydrocarbyl)thiocarbamate intermediate to provide product dithiocarbamyl carboxylic acid.

In Step 3 of Procedure A, the dithiocarbamyl carboxylic acid intermediate is reacted with molybdenum trioxide to provide the molybdenum dithiocarbamyl carboxylic acid product.

The molybdenum dithiocarbamyl carboxylic acid compounds of this invention can also be prepared in accordance with the following sequence of reaction steps in Procedure B below:

Procedure B:

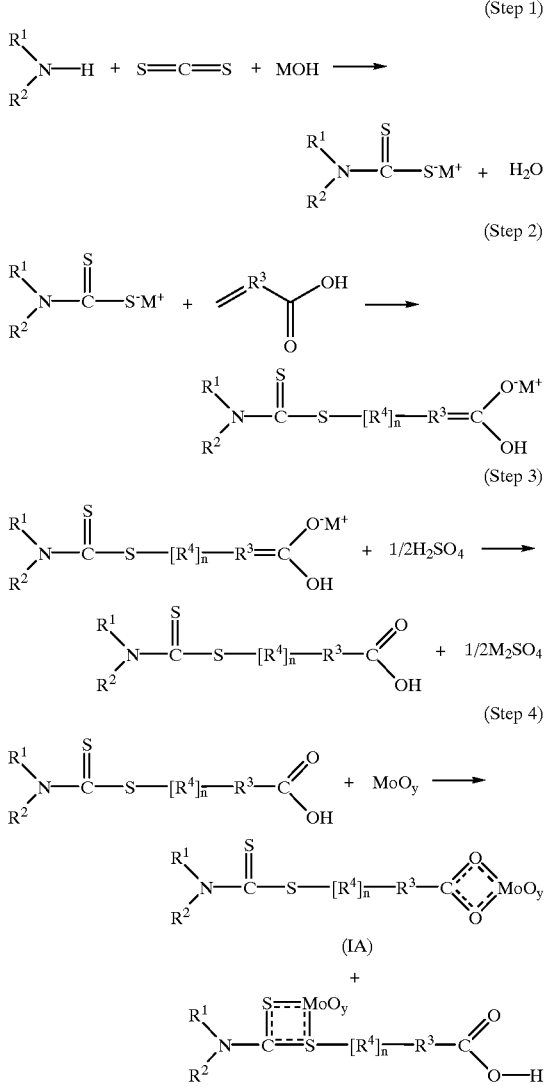

$R^1$, $R^2$, $R^3$, $R^4$, n and y are each as defined above, M is an alkali metal, such as sodium, and X is halogen, preferably chlorine.

In step 1 of Procedure B, the dihydrocarbylamine $R^1R^2NH$ is reacted with an equimolar amount of alkali metal hydroxide MOH and carbon disulfide, the latter preferably in slight molar excess, to provide an alkali metal di(hydrocarbyl)thiocarbamate intermediate $R^1R^2NCSSM$. Useful dihydrocarbylamines are those in which hydrocarbyl groups $R^1$ and $R^2$ are selected from among alkyl, cycloalkyl, alkaryl and aralkyl groups of up to about 60 carbon atoms. Preferred dihydrocarbylamine reactants are dialkylamines in which each alkyl group contains from about 2 to about 30, and more preferably from about 4 to about 24, carbon atoms. The alkali metal hydroxide can be, e.g., aqueous sodium hydroxide and the reaction can be advantageously conducted in a suitable solvent with water and/or a lower alkanol such as methanol, ethanol, propanol, 2-propanol, n-butanol, sec-butanol, t-butanol, or preferably, isopropanol.

In Step 2 of Procedure B, the alkali metal di(hydrocarbyl) thiocarbamate intermediate of Step 1 is reacted with an equimolar amount of acrylic acid to form an alkali metal di(hydrocarbyl)thiocarbamyl acid intermediate $R^1R^2NCSS(R^4)_nR^3COOH^-M^+$.

In Step 3 of Procedure B, the alkali metal di(hydrocarbyl) thiocarbamate intermediate of Step 2 is reacted with a one-half molar equivalent of sulfuric acid to form a one-half molar equivalent of sodium sulfate and a one molar equivalent of a dithiocarbamyl carboxylic acid intermediate $R^1R^2NCSS(R^4)_nR^3COOH$.

In Step 4 of Procedure B, dithiocarbamyl carboxylic acid intermediate of Step 3 is reacted with molybdenum trioxide to provide the molybdenum dithiocarbamyl carboxylic acid product.

The molybdenum dithiocarbamyl amide compounds of formula IB and the dithiocarbamyl amide compounds of formula IC, can be prepared in accordance with the following sequence of reaction steps in Procedure C below.

Procedure C:

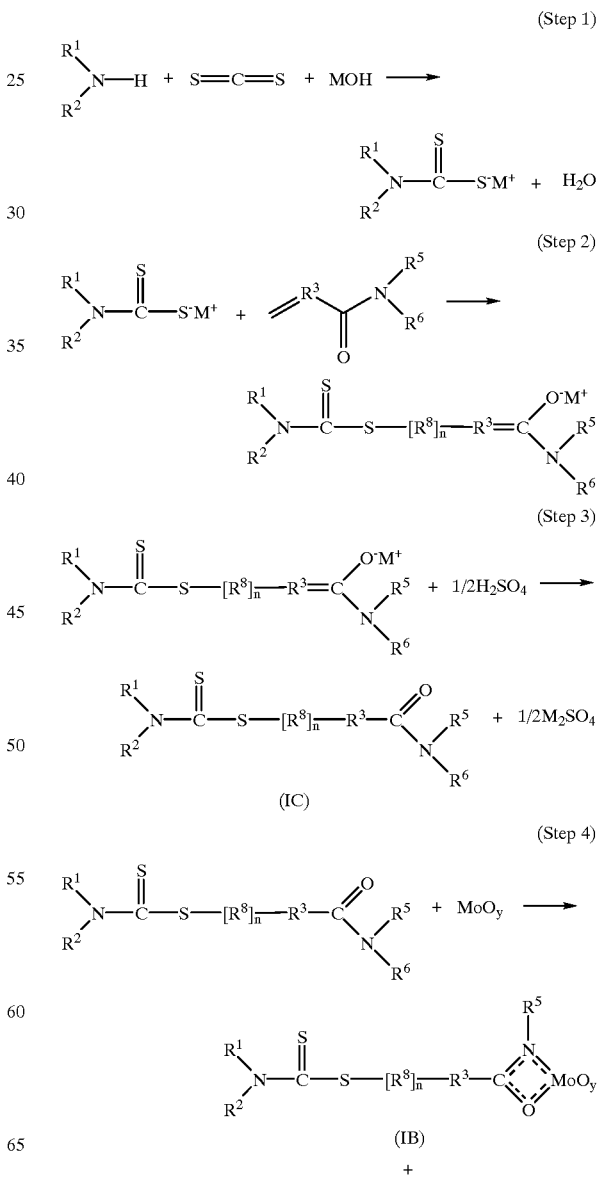

-continued

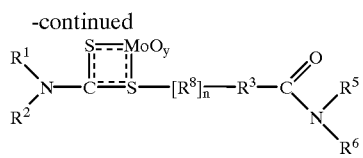

$R^1$, $R^2$, $R^3$, $R^5$, $R^6$, $R^8$, n and y are each as defined above, and M is an alkali metal, such as sodium.

In Step 1 of Procedure C, the dihydrocarbylamine $R^1R^2NH$ is reacted with an equimolar amount of an alkali metal hydroxide MOH and carbon disulfide, the latter preferably in slight molar excess, to provide an alkali metal di(hydrocarbyl)thiocarbamate intermediate $R^1R^2NCSSM$. Useful dihydrocarbylamines are those in which hydrocarbyl groups $R^1$ and $R^2$ are selected from among alkyl, cycloalkyl, alkaryl and aralkyl groups of up to about 60 carbon atoms. Preferred dihydrocarbylamine reactants are dialkylamines in which each alkyl group contains from about 2 to about 30, and more preferably from about 4 to about 24, carbon atoms. The alkali metal hydroxide can be, e.g., aqueous sodium hydroxide and the reaction can be advantageously conducted in a suitable solvent with water and/or a lower alkanol such as methanol, ethanol, propanol, 2-propanol, n-butanol, sec-butanol, t-butanol, or preferably, isopropanol.

In Step 2 of Procedure C, the alkali metal di(hydrocarbyl) thiocarbamate intermediate of Step 1 is reacted with an equimolar amount of an acrylamide to form an alkali metal di(hydrocarbyl)thiocarbamyl amide intermediate $R^1R^2NCSS(R^8)_n R^3CO^-M^+NR^5R^6$.

In Step 3 of Procedure C, the alkali metal di(hydrocarbyl) thiocarbamate amide intermediate of Step 2 is reacted with a one-half molar equivalent of sulfuric acid to form a one-half molar equivalent of alkali metal sulfate and a one molar equivalent of a dithiocarbamyl amide of formula IC.

In Step 4 of Procedure C, the dithiocarbamyl amide compound of formula IC produced in Step 3 is reacted with molybdenum trioxide to provide the molybdenum dithiocarbamyl amide compound of formula IB.

The dithiocarbamyl amide compounds of formula ID and the molybdenum dithiocarbamyl amide compounds of formula IE, can be prepared in accordance with the following sequence of reaction steps in Procedure D below.

Procedure D:

(Step 1)

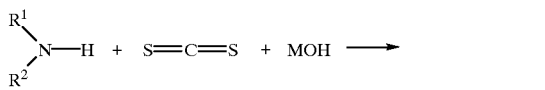

(Step 2)

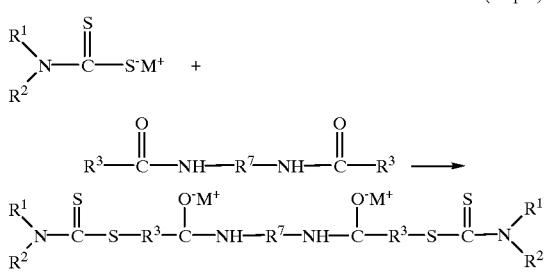

(Step 3)

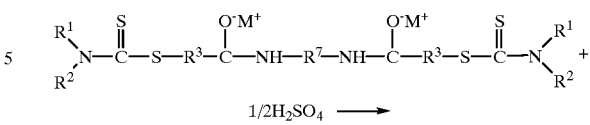

$1/2 H_2SO_4 \longrightarrow$

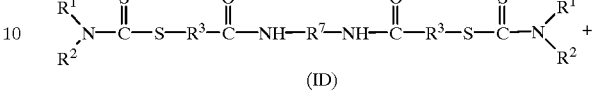
(ID)

$1/2 M_2SO_4$ (Step 4)

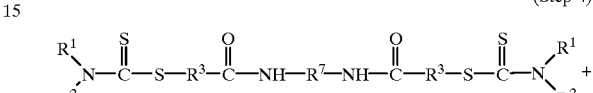
(ID)

$MoO_y \longrightarrow$

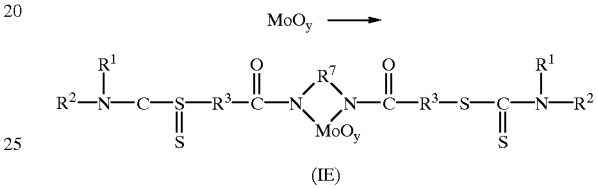
(IE)

In step 1 of Procedure D, the dihydrocarbylamine $R^1R^2NH$ is reacted with an equimolar amount of alkali metal hydroxide MOH and carbon disulfide, the latter preferably in slight molar excess, to provide an alkali metal di(hydrocarbyl)thiocarbamate intermediate $R^1R^2NCSSM$. Useful dihydrocarbylamines are those in which hydrocarbyl groups $R^1$ and $R^2$ are selected from among alkyl, cycloalkyl, alkaryl and aralkyl groups of up to about 60 carbon atoms. Preferred dihydrocarbylamine reactants are dialkylamines in which each alkyl group contains from about 2 to about 30, and more preferably from about 4 to about 24, carbon atoms. The alkali metal hydroxide can be, e.g., aqueous sodium hydroxide and the reaction can be advantageously conducted in a suitable solvent with water and/or a lower alkanol such as methanol, ethanol, propanol, 2-propanol, n-butanol, sec-butanol, t-butanol, or preferably, isopropanol.

In Step 2 of Procedure D, the alkali metal di(hydrocarbyl) thiocarbamate intermediate of Step 1 is reacted with an equimolar amount of a bis-acrylamide to form an alkali metal N,N'-di(hydrocarbyl)thiocarbamyl amide intermediate $R^1R^2NC(S)SR^3C(O^-M^+)NH-R^7-NHC(O^-M^+)R^3SC(S)NR^1R^2$.

In Step 3 of Procedure D, the alkali metal N,N'-di (hydrocarbyl)thiocarbamate amide intermediate of Step 2 is reacted with a one-half molar equivalent of sulfuric acid to form a one-half molar equivalent of alkali metal sulfate and a one molar equivalent of the N,N'-dithiocarbamyl amide of formula ID.

In Step 4 of Procedure D, the N,N'-dithiocarbamyl amide compound of formula ID produced in Step 3 is reacted with molybdenum trioxide to provide the molybdenum N,N' dithiocarbamyl amide compound of formula IE.

The dithiocarbamyl compounds of this invention can be utilized in lubricating oil compositions in amounts which impart anti-wear characteristics to the oils as well as reducing the friction of engines operating with the oils. Concentrations of from about 0.001 to about 10 weight percent based on the total weight of the lubricating oil composition can be used. Preferably, the concentration is from about 0.1 to about 3 weight percent.

In general, mineral oils, both paraffinic, naphthenic and mixtures thereof, including those oils defined as American Petroleum Institute Groups I, II, and III, can be employed as the lubricant vehicle, and can be of any suitable lubricating viscosity range, as for example, from about 2 cSt at 100° C. to about 1,000 cSt at 100° C. and preferably from about 2 to about 100 cSt at 100° C. These oils can have viscosity indexes preferably ranging from about 80 to about 180. The average molecular weights of these oils can range from about 250 to about 800. Where synthetic oils are employed, they can include, e.g., polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, and phenoxy phenylethers.

The dithiocarbamyl compounds of this invention can be utilized in lubricating oil compositions in combination with other additives, such as, e.g., anti-wear agents, corrosion inhibitors, extreme pressure agents, detergents, dispersants, antiwear agents, antioxidants, antifoamants, friction modifiers, low temperature properties modifiers, and the like. See, e.g., U.S. Pat. No. 5,498,809 for a description of useful lubricating oil composition additives. Examples of these materials include metallic phenates or sulfonates, alkylated diphenylamines, polymeric succinimides, non-metallic or metallic phosphorodithioates such as the zinc dialkyl dithiophosphates, and the like.

The following examples are provided to illustrate the present invention.

EXAMPLES

Example 1

Preparation of 3-(N,N-ditetradecyldithiocarbamyl)-propionic Acid Molybdenum Complex (Compound No. 1)

Step 1: Preparation of Sodium N,N-ditetradecyldithiocarbamate

To a 500 mL 3-neck round bottom reaction flask equipped with an overhead stirrer, a thermocouple probe, a reflux condenser, a Claisen adapter, and a 25 mL addition funnel, 82.0 g (0.20 mol) of dicoco amine (Armeen 2C, AKZO), 16.2 g of a 50 weight percent NaOH solution (0.20 mol NaOH) and 100 mL reagent 2-propanol was added. 13.0 mL (0.22 mol) carbon disulfide was charged to the addition funnel. The reactor was heated to 50° C. Once the amine was dissolved, the reaction temperature was reduced to 40° C. Carbon disulfide was added over a half-hour period. The reaction temperature was lowered over the course of the carbon disulfide addition from 40° C. to 30° C. The product was post-reacted at 30° C. for 1 hour.

Step 2: Preparation of 3-(N,N-ditetradecyldithiocarbamyl)-propionic Acid Intermediate 21.7 g (0.20 mol) of 3-chloropropionic acid was added to the reactor containing the Step 1 product. The reactor was heated to reflux with the pot temperature maintained at 74° C. for 3 hours. The reaction temperature was then reduced to 30° C. The product was transferred to a 1000 mL separatory funnel, combined with 100 mL reagent hexanes, and washed four times with 300 mL portions of 60° C. water. The volatiles were removed using a rotary evaporator. 98.8 g of 3-(N,N-ditetradecyldithiocarbamyl)-propionic acid as a light yellow product was obtained having a consistency of petroleum jelly at room temperature.

Step 3: Preparation of the Molybdenum Complex 19.3 grams of 3-(N,N-ditetradecyldithio-carbamyl)-propionic acid from step 2 were combined with 25 mL reagent hexanes and 2.5 grams $MoO_3$ in a 100 mL 3-neck flask equipped with a reflux condenser, overhead stirrer and a thermocouple probe. The system was heated to reflux, pot temp 69° C., and maintained for 4 hours. The reaction was cooled and the unreacted solid was filtered off. The volatiles were removed using a rotary evaporator, to produce 19.8 grams of 3-(N,N-ditetradecyldithiocarbamyl)propionic acid molybdenum complex (19.8 g) as a dark brown liquid.

Elemental analysis: % Mo=2.50, % S=8.20, % N=2.95.

Example 2

Preparation of 3-(N,N-di-(2-ethylhexyl)-dithiocarbamyl)-propionic Acid Molybdenum Complex (Compound No. 2)

Step 1: Preparation of the Sodium di(2-ethylhexyl)-dithiocarbamate Salt 50.0 grams (0.207 mol) of di(2-ethylhexyl)amine, 16.9 grams of a 50 wt % NaOH solution (0.211 mol NaOH), and 60 mL reagent 2-propanol were combined in a 250 mL 3-neck round bottom reaction flask equipped with an overhead stirrer, a thermocouple probe, a reflux condenser, a Clasien adapter and a 25 mL addition funnel. 12.7 mL (0.211 mol) carbon disulfide was charged into the addition funnel. Carbon disulfide was added dropwise over a 30 minute period. The reaction temperature was maintained at 20–25° C. over the course of the $CS_2$ addition. The product was post-reacted at 25° C. for six hours.

Step 2: Preparation of the Propionic Acid Derivative 22.5 grams (0.207 mol) of 3-chloropropionic acid was added to the reactor containing the product of Step 1. The reaction mixture so formed was heated to reflux, pot temperature 74° C., and maintained for 5 hours. The reaction mixture was then cooled to 30° C. The reaction mixture was then transferred to a 500 mL separatory funnel along with 100 mL reagent xylenes and washed four times with 200 mL portions of 60° C. water. The organic layer in the separatory funnel was then transferred back into the 250 mL 3-neck reactor system.

Step 3: Preparation of the Molybdenum Complex 14.8 grams (0.103 mol) MoO3 was added to the reactor containing the product of Step 2. The resultant reaction mixture was heated to reflux, pot temp 108° C., and maintained for 2 hours. The reaction mixture was cooled and the unreacted solid was filtered off. The volatiles were removed from the reaction mixture using a rotary evaporator, to produce 70.5 grams of 3-(N,N-di-(2-ethylhexyl)-dithiocarbamyl)-propionic acid molybdenum complex (70.5 g) as a medium brown liquid.

Elemental analysis: % Mo=1.09, % S=13.19, % N=6.64.

Example 3

Preparation of 3-(N,N-di-(2-ethylhexyl)-dithiocarbamyl)-propionic Acid Molybdenum Complex (Compound No. 3)

Step 1: Preparation of the Sodium di(2-ethylhexyl)-dithiocarbamate salt 50.0 grams (0.207 mol) of di(2-ethylhexyl)amine, 16.9 grams of a 50 wt % NaOH solution (0.211 mol NaOH), and 60 mL reagent 2-propanol were combined in a 250 mL 3-neck round bottom reaction flask equipped with an overhead stirrer, a thermocouple probe, a reflux condenser, a Clasien adapter and a 25 mL addition funnel. 12.7 mL (0.211 mol) carbon disulfide was added to the addition funnel dropwise over a 30 minute period. The reaction temperature was maintained at 20–25° C. over the course of the $CS_2$ addition. The product was post-reacted at 25° C. for 1.5 hours.

Step 2: Preparation of the Propionic Acid Derivative 22.5 grams (0.207 mol) of 3-chloropropionic acid was added to the reactor containing the product of Step 1. The reaction mixture so formed was heated to reflux, pot temperature 74° C., and maintained for 3.5 hours. The reaction mixture was then cooled to 30° C. The cooled reaction mixture was then transferred to a 500 mL separatory funnel along with 100 mL reagent xylenes and then washed five times with 200 mL portions of 70° C. water. The organic layer in the separatory funnel was then transferred into the 250 mL 3-neck reactor system.

Step 3: Preparation of the Molybdenum Complex 5.0 grams (0.035 mol) $MoO_3$ was added to the reactor containing the product of Step 2. A Dean-Stark water trap was installed between the reactor and the reflux condenser. The reaction mixture so formed was heated to reflux and the volatiles removed until xylene reflux temperature was reached, pot temp 143° C. The 143° C. temperature was maintained for 5 hours. The reaction mixture was cooled, unreacted solids were filtered off, and volatiles were removed using a rotary evaporator, to produce 3-(N,N-di-(2-ethylhexyl)-dithiocarbamyl)-propionic acid molybdenum complex (62.6 g) as a medium brown liquid.

Elemental analysis: % Mo=0.41, % S=7.78, % N=4.34.

Example 4

Preparation of 3-(N,N-di-(2-ethylhexyl)-dithiocarbamyl)-propionic Acid Molybdenum Complex (Compound No. 4)

Step 1: Preparation of the Sodium di(2-ethylhexyl)-dithiocarbamate salt 50.0 grams (0.207 mol) of di(2-ethylhexyl)amine, 16.9 grams of a 50 wt % NaOH solution (0.211 mol NaOH), and 60 mL reagent 2-propanol were combined in a 250 mL 3-neck round bottom reaction flask equipped with an overhead stirrer, a thermocouple probe, a reflux condenser, a Clasien adapter and a 25 mL addition funnel. 12.7 mL (0.211 mol) carbon disulfide was charged to the addition funnel dropwise over a 30 minute period. The reaction temperature was maintained at 20–25° C. over the course of the $CS_2$ addition. The resultant reaction product was post-reacted at 25° C. for 1.5 hours.

Step 2: Preparation of the Propionic Acid Derivative 22.5 grams (0.207 mol) of 3-chloropropionic acid was added to the reactor containing the product of Step 1. The resultant reaction mixture was heated to reflux, pot temperature 71° C., and maintained for 4 hours. The reaction mixture was then cooled reaction to 30° C. The cooled reaction mixture was then transferred to a 500 mL separatory funnel along with 100 mL reagent xylenes and washed five times with 200 mL portions of 70° C. water. The organic layer in the separatory funnel was transferred into the 250 mL 3-neck reactor system.

Step 3: Preparation of the Molybdenum Final Product 5.0 grams (0.035 mol) $MoO_3$ and 10 mL deionized (DI) water were added to the reactor containing the product of Step 2. The resultant reaction mixture was then heated to reflux., pot temperature 97° C. and maintained for 6 hours. The reaction mixture was cooled and the unreacted solids were filtered off. The volatiles were then removed from the reaction mixture using a rotary evaporator, to produce 3-(N,N-di-(2-ethylhexyl)dithiocarbamyl)propionic acid molybdenum complex (74.0 g) as a medium brown liquid.

Elemental analysis: % Mo=3.43, % S=12.81, % N=3.77.

Example 5

Preparation of 3-(N,N-di-(2-ethylhexyl)-dithiocarbamyl)-propionic Acid Molybdenum Complex (Compound No. 5)

Step 1: Preparation of the Sodium di(2-ethylhexyl) dithiocarbamate Salt 313.6 grams (1.300 mol) of di(2-ethylhexyl)amine, 106.1 grams of a 50 wt % NaOH solution (1.326 mol NaOH), and 230 mL reagent 2-propanol were combined in a 2 liter bottom-out resin kettle reaction flask equipped with an overhead stirrer, a thermocouple probe, a reflux condenser, a Clasien adapter and a 125 mL addition funnel. 79.8 mL (1.326 mol) carbon disulfide were charged dropwise to the addition funnel over a 30 minute period. The reaction temperature was maintained at 20–25° C. over the course of the $CS_2$ addition. The resultant reaction product was post-reacted at 25° C. for 2 hours.

Step 2: Preparation of 3-(N,N-di-(2-ethylhexyl) dithiocarbamyl)-propionic Acid 89.1 mL (1.300 mol) of acrylic acid were charged to the 125 mL addition funnel (after cleaning) and 230 mL deionized ("DI") water to the reactor containing the reaction product of Step 1. The acrylic acid was added dropwise over a 30 minute period. The reaction temperature was maintained at 25–30° C. The resultant reaction mixture was post-reacted at 35° C. for 6 hours and then cooled to 5° C. 37.3 mL (0.664 mol) concentrated sulfuric acid was then added to the cooled reaction mixture over a 45 minute period. The temperature of the reaction mixture rose to 10° C. 500 mL reagent butyl acetate was then added to the reaction mixture and the reaction mixture was post-reacted at 18° C. for 1 hour. The resultant product was washed four times with 200 mL of 60° C. DI water each wash. A Dean-Stark moisture trap was installed between the reactor and reflux condenser. The reaction mixture was heated to reflux and all volatiles were removed until butyl acetate reflux temperature was reached. The reaction mixture was then cooled to 65° C.

Step 3: Preparation of the Molybdenum Complex 18.7 grams of $MoO_3$ was added to the reaction mixture produced in Step 2 along with 65 mL DI water. The reaction mixture was then heated to reflux, pot temperature 91° C., and maintained for 6 hours. The reaction mixture was filtered to remove unreacted solids. The volatiles were then removed from the reaction mixture using a rotary evaporator, to produce 3-(N,N-di-(2-ethylhexyl) dithiocarbamyl)propionic acid molybdenum complex (479 g) as a dark brown liquid.

Elemental analysis: % Mo=2.17, % S=8.90, % N=7.90.

Example 6

Preparation of 3-(N,N-di(2-ethylhexyl) dithiocarbamyl)-propionamide (Compound No. 6)

Step 1: Preparation of the Sodium di(2-ethylhexyl) dichiocarbamate Salt 72.4 grams (0.030 mole) of di(2-ethylhexyl)amine, 24.5 grams (0.31 mole) of a 50 wt % NaOH solution, and 60 ml of reagent 2-propanol were added to a 500 ml 3-neck round-bottom reaction flask equipped with an overhead stirrer, thermocouple probe, clasien adapter, 25 ml addition funnel and a reflux condenser. 18.4 ml (0.31 mole) of carbon disulfide was then charged to the addition funnel over a 30 minute period. The reaction temperature was maintained at 18–22° C. over the course of the $CS_2$ addition. The resultant reaction product was post-reacted at 23° C. for 5 hours.

Step 2: Preparation of the Sodium Dithiocarbamyl Proprionamide Salt 21.3 grams (0.30 mol) acrylamide was dissolved in 40 mL deionized water and then charged to to a 100 mL addition funnel. The acrylamide was then added to the reaction product over a 30 minute period. The addition temperature was 40° C. The resultant reaction mixture was post-reacted at 40° C. for 4.5 hours and then cooled to 4–5° C. 0.153 mol concentrated sulfuric acid was then added to the cooled reaction mixture over a 30 minute period. The addition temperature was 5–10° C. 60 mL reagent xylenes was then added to the reaction mixture and the resultant reaction mixture was heated at 40° C. for 2 hours. The resultant product was washed three times with 100 mL of 60° C. DI water each wash. The volatiles were removed from the washed reaction product using a rotary evaporator, to produce 100.9 grams of 3-(N,N-di(2-ethylhexyl) dithiocarbamyl)-propionamide as a medium yellow, low viscosity liquid.

Example 7

Preparation of 3-(N,N-di(2-ethylhexyl) dithiocarbamyl)-propionamide Molybdenum Complex (Compound No. 7)

25.7 grams (0.066 mol) of 3-(N,N-di(2-ethylhexyl) dithiocarbamyl)-propionamide (Example 6), 0.95 grams of molybdenum trioxide (0.007 mol), 20 mL reagent xylenes and 5 mL DI water were added to a 100 mL 3-neck reaction flask equipped with an overhead stirrer, a reflux condenser, and a thermocouple probe, and heated to reflux at a pot temperature of 97° C. for 7 hours. The reaction mixture was then cooled and filtered. The volatiles were then removed from the reaction mixture using a rotary evaporator, to produce 24.7 grams of 3-(N,N-di(2-ethylhexyl) dithiocarbamyl)propionamide molybdenum complex as a dark green viscous liquid.

Elemental analysis: % Mo=2.47, % S=11.94, % N=7.15

Example 8

Preparation of 3-(N,N-di(2-ethylhexyl) dithiocarbamyl)-propionamide Molybdenum Complex (Compound No. 8)

25.5 grams (0.066 mol) of 3-(N,N-di(2-ethylhexyl) dithiocarbamyl)-propionamide (Example 6), 2.8 grams of molybdenum trioxide (0.02 mol), 20 mL reagent xylenes and 5 mL DI water were added to a 100 mL 3-neck reaction flask equipped with an overhead stirrer, a reflux condenser, and a thermocouple probe, and heated to reflux at a pot temperature of 96° C. for 1 hour. The reaction mixture was then cooled and filtered. The volatiles were removed from the reaction mixture using a rotary evaporator, to produce 27.8 grams of 3-(N,N-di(2-ethylhexyl)dithiocarbamyl) propionamide molybdenum complex as a dark green viscous liquid.

Elemental analysis: % Mo=6.21, % S=12.40, % N=6.00

Example 9

Preparation of 3-(N,N-di(2-ethylhexyl) dithiocarbamyl)-propionamide Molybdenum Complex (Compound No. 9)

Step 1: Preparation of the Sodium di(2-ethylhexyl) dichiocarbamate Salt 325.6 grams (1.350 mol) of di(2-ethylhexyl)amine, 114.1 grams of a 50 wt % NaOH solution (1.427 mol NaOH), and 270 ml of reagent 2-propanol were added to a 2 liter bottom-out resin kettle reaction flask equipped with an overhead stirrer, thermocouple probe, a reflux condenser, Clasien adapter, and a 125 mL addition funnel. 82.9 ml (1.377 mole) of carbon disulfide was then charged to the addition funnel dropwise over a 30 minute period. The reaction temperature was maintained at 20–25° C. over the course of the $CS_2$ addition. The resultant reaction product was post-reacted at 25° C. for 1 hour.

Step 2: Preparation of the Sodium Dithiocarbamyl Proprionamide Salt 96.9 grams (1.364 mol) acrylamide was dissolved in 400 mL DI water and then charged to to a 500 mL addition funnel. The acrylamide was then added to the reaction product of Step 1 over a 30 minute period. The addition temperature was 22–25° C. The resultant reaction mixture was post-reacted at 25° C. for 6 hours and then cooled to 5° C.

Step 3: Preparation of the 3-(N,N-di(2-ethylhexyl) dithiocarbamyl)propionamide intermediate 74 grams (0.717 mol) of concentrated sulfuric acid was then added to the cooled reaction product of Step 2 over a 45 minute period. The reaction temperature rose to 14° C. 500 mL of reagent xylenes was then added to the reaction mixture and the resultant reaction mixture was post-reacted at 22° C. for 1 hour. The resultant product was washed three times with 200 mL of 60° C. DI water each wash. A Dean-Stark moisture trap was installed between the reactor and the reflux condenser. The washed reaction product was then heated to reflux to remove to all volatiles until xylene reflux temperature was reached. The reaction product was then cooled to 65° C.

Step 4: Preparation of the Molybdenum Complex 58.3 grams of $MoO_3$ and 78 mL DI water were added to the reaction product of Step 3 and heated to reflux at a pot temperature of 90° C. for 3 hours. The volatiles were removed from the reaction mixture using a rotary evaporator, to produce 545.0 grams of 3-(N,N-di(2-ethylhexyl)dithiocarbamyl)propionamide molybdenum complex as a dark green liquid.

Elemental analysis: % Mo=6.37, % S=6.39, % N=6.19

Example 10

Preparation of 3-(N,N-di(2-ethylhexyl) dithiocarbamyl)-propionamide Molybdenum Complex (Compound No. 10)

Step 1: Preparation of the Sodium di(2-ethylhexyl) dichiocarbamate Salt 325.6 grams (1.350 mol) of di(2-ethylhexyl)amine, 110.2 grams of a 50 wt % NaOH solution (1.377 mol NaOH), and 250 ml of reagent 2-propanol were added to a 2 liter bottom-out resin kettle reaction flask equipped with an overhead stirrer, thermocouple probe, a reflux condenser, Clasien adapter, and a 125 mL addition funnel. 82.9 ml (1.377 mole) of carbon disulfide was then charged to the addition funnel dropwise over a 30 minute period. The reaction temperature was maintained at 20–25° C. over the course of the $CS_2$ addition The resultant reaction product was post-reacted at 25° C. for 2 hours.

Step 2: Preparation of the Sodium Dithiocarbamyl Proprionamide Salt 96.9 grams (1.364 mol) acrylamide was dissolved in 400 mL DI water and then charged to to a 500 mL addition funnel. The acrylamide was then added to the reaction product of Step 1 over a 30 minute period. The addition temperature was 25–30° C. The resultant reaction mixture was post-reacted at 25° C. for 6 hours and then cooled to 5° C.

Step 3: Preparation of the 3-(N,N-di(2-ethylhexyl) dithiocarbamyl)propionamide Intermediate 71.3 grams (0.690 mol) of concentrated sulfuric acid was then added to the cooled reaction product of Step 2 over a 45 minute period. The reaction temperature rose to 14° C. 400 mL of reagent xylenes was then added to the reaction mixture and the resultant reaction mixture was post-reacted at 22° C. for 1 hour. The resultant product was washed three times with 200 mL of 60° C. DI water each wash. A Dean-Stark moisture trap was installed between the reactor and the reflux condenser. The washed reaction product was then heated to reflux to remove to all volatiles until xylene reflux temperature was reached. The reaction product was then cooled to 65° C.

Step 4: Preparation of the Molybdenum Complex 58.3 grams of $MoO_3$ and 78 mL DI water were added to the reaction product of Step 3 and heated to reflux at a pot temperature of 90° C. for 3 hours. The volatiles were removed from the reaction mixture using a rotary evaporator, to produce 544.2 grams of 3-(N,N-di(2-ethylhexyl)dithiocarbamyl)propionamide molybdenum complex as a dark green liquid.

Elemental analysis: % Mo=7.46, % S=13.12, % N=6.05

Example 11

Preparation of Glyoxal bis N,N'-(di-(2-ethylhexyl)-dithiocarbamyl) Propionamide Molybdenum Complex (Compound No. 11)

Step 1: Preparation of the Sodium di(2-ethylhexyl) dithiocarbamate Salt.

149.2 grams (0.62 mol) of di(2-ethylhexyl)amine, 50.5 grams of a 50 wt % NaOH solution (0.63 mol NaOH), and 80 mL reagent 2-propanol, were all added to a 1 liter bottom-out resin kettle reaction flask equipped with an overhead stirrer, a thermocouple probe, a reflux condenser, a Clasien adapter and a 60 mL addition funnel. 37.9 mL (0.63 mol) of carbon disulfide ($CS_2$) was then charged to the addition funnel and added dropwise over a 30 minute period. The reaction temperature was maintained at 18–20° C. over the course of the $CS_2$ addition. The resultant reaction mixture was post-reacted at 30° C. for 1 hour.

Step 2: Preparation of Glyoxal bis N,N'-(di-(2-ethylhexyl) dithiocarbamyl)propionamide Sodium Salt.

61.9 grams (0.31 mol) of glyoxal bis acrylamide were added to the reaction product of Step 1 and heated at 40° C. for 2 hours.

Step 3: Preparation of the Glyoxal bis N,N'-(di-(2-ethylhexyl)dithiocarbamyl)propionamide intermediate.

The resultant reaction product of Step 2 was cooled to 15° C. 200 mL reagent xylenes were then added to the cooled reaction product followed by the addition of 33.5 grams (0.32 mol) of concentrated sulfuric acid over a 15 minute period. The reaction temperature rose to 20° C. The resultant reaction mixture was post-reacted at 20° C. for 30 minutes and then at 40° C. for 2 hours. The resultant reaction product was washed one time with 300 mL of 70° C. DI water. A Dean-Stark moisture trap was then installed between the reactor and reflux condenser. To remove the volatiles, the reaction product was then heated to reflux until the xylene reflux temperature was reached. The reaction product was then cooled to 85° C.

Step 4: Preparation of the Molybdenum Complex.

25.6 grams of $MoO_3$ were added to the resultant reaction product of Step 4 along with 45 mL DI water (pH adjusted to 2 using sulfuric acid). The resultant reaction mixture was heated to reflux for 2.5 hours, pot temperature 93° C.

The warm reaction mixture was filtered through a 1 micron filter. The volatiles were removed from the filtered reaction mixture using a rotary evaporator to produce 242 grams of glyoxal bis N,N'-(di-(2-ethylhexyl)dithiocarbamyl) propionamide molybdenum complex as a dark green liquid.

Elemental analysis: % Mo=6.37.

Example A

Four-ball Anti-wear Test

The SAE 10W-30 motor oil formulations described in Table 1 below were prepared.

TABLE 1

| SAE 10W-30 Motor Oil Formulations | | |
|---|---|---|
| Ingredient | A (wt. %) | B (wt. %) |
| Solvent Neutral 100 | 22.8 | 22.8 |
| Solvent Neutral 150 | 60 | 60 |
| Succinimide Dispersant | 7.5 | 7.5 |
| Overbased Calcium Phenate Detergent | 2.0 | — |
| Overbased Calcium Sulfonate Detergent | — | 2.0 |
| Neutral Calcium Sulfonate Detergent | 0.5 | 0.5 |
| Alkylated Diphenylamine Antioxidant | 0.5 | 0.5 |
| Rust Inhibitor | 0.1 | 0.1 |
| Pour Point Depressant | 0.1 | 0.1 |
| OCP VI Improver | 5.5 | 5.5 |

Compounds 1–10 were tested in the oil compositions described below in Table 2 in a Four-Ball Wear Test as described in ASTM D4172. The results of this testing are also included in Table 2.

TABLE 2

| Four-Ball Wear Test Results | | | |
|---|---|---|---|
| Oil Composition[1] | Compound (1 wt. %) | Formulation[1] (99 wt. %) | Wear Scar Diameter (mm) |
| 1 | 1 | A | 0.37 |
| 2 | 2 | A | 0.35 |
| 3 | 3 | A | 0.35 |
| 4 | 4 | A | 0.33 |
| 5 | 6 | A | 0.46 |
| 6 | 7 | A | 0.49 |
| I | None[2] | A | 0.93 |
| II | ZZDP[3] | A | 0.46 |
| 7 | 2 | B | 0.59 |
| 8 | 4 | B | 0.61 |
| 9 | 6 | B | 0.60 |
| 10 | 7 | B | 0.58 |
| III | None[2] | B | 0.98 |
| IV | ZDDP[3] | B | 0.53 |
| 11 | 8 | A | 0.59 |
| 12 | 8 | B | 0.49 |
| 13 | 9 | A | 0.71 |
| 14 | 9 | B | 0.51 |
| 15 | 10 | B | 0.56 |
| 25 | 11 | A | 0.53 |
| 26 | 11 | B | 0.73 |

[1]The fully formulated oil compositions tested also contained 1 wt % cumene hydroperoxide to help simulate the environment of a running engine.
[2]1 wt % of solvent neutral 150 added instead of a compound
[3]Zinc dialkyldithiophosphate

Example B

Cameron-Plint TE77 High Frequency Friction Machine Anti-Wear Test

For each test, the test parts (6 mm diameter AISI 52100 steel balls of 800±20 kg/mm$^2$ hardness and hardened ground NSOH B01 gauge plates of RC 60/0.4 microns) were rinsed and then sonicated for 15 minutes with technical grade hexanes. This procedure was then repeated with isopropyl alcohol. The test parts were then dried with nitrogen and set into a Cameron-Plint TE77 High Frequency Friction Machine ("TE77"). The oil bath in the TE77 was then filled with 10 mL of one of the compositions listed in Table 3 below. Each test was run at a 30 Hertz Frequency, 100 Newton Load, 2.35 mm Amplitude. At the start of each test the test parts and the test composition was at room temperature. Immediately the temperature was ramped over 15 minutes to 50° C., where it remained for an additional 15 minutes. The temperature was then ramped over 15 minutes to 100° C., where it remained for an additional 45 minutes. Finally, the temperature was then ramped over 15 minutes to 150° C. and held there for an additional 15 minutes. The total length of time of each test was 2 hours. At the end of each test, the wear scar diameter on the 6 mm ball was measured using a Leica StereoZoom6® Stereomicroscope and a Mitutoyo 164 series Digimatic Head. The anti-wear test results for each tested composition are presented in Table 3 below. In Table 3 the numerical value of the Wear Scar Diameter in mm decreases with an increase in anti-wear effectiveness of the composition tested.

TABLE 3

Cameron-Plint TE77 High Frequency Friction Machine Anti-Wear Test Results

| Oil Composition[1] No.[1] | Compound (1 wt. %) | Formulation[1] (99 wt. %) | Wear Scar Diameter (mm) |
|---|---|---|---|
| 1 | 1 | A | 0.52 |
| 2 | 2 | A | 0.51 |
| 3 | 3 | A | 0.57 |
| 4 | 4 | A | 0.40 |
| I | None[2] | A | 0.66 |
| II | ZDDP[3] | A | 0.46 |
| 7 | 2 | B | 0.51 |
| 8 | 4 | B | 0.46 |
| III | None[2] | B | 0.67 |
| IV | ZDDP[3] | B | 0.54 |
| 5 | 6 | B | 0.64 |
| 11 | 8 | A | 0.50 |
| 12 | 8 | B | 0.42 |

[1]The fully formulated oil compositions tested also contained 1 wt % cumene hydroperoxide to help simulate the environment of a running engine.
[2]1 wt % of Solvent Neutral 150 added instead of a compound
[3]Zinc dialkyldithiophosphate

Example C

Pressure Differential Scanning Calorimetry ("PDSC") Oxidation Stability Test The oil compositions described in Table 4 were tested for oxidation stability. The compositions were blended at 65° C. for 15 minutes under a nitrogen atmosphere.

The instrument used for this test was a Mettler DSC27HP (Mettler-Toledo, Inc.) 3 mg of each composition listed in Table 4 below was added to an open aluminum pan along with 50 ppm soluble iron derived from iron naphthanate (catalyst), and placed into the steel bomb of the Mettler DSC27HP. The pressure in the steel bomb was increased to 500 psi and the steel bomb was then heated at a rate of 40° C./min to isothermal temperature of 175° C. The flow of oxygen through the cell was 100 ml/min. The induction time was measured from the time the sample reaches 175° C. until the enthalpy change was measured and recorded by an electric signal. The results of this test are presented below in Table 4. The longer the oxidation induction time, the better the oxidation stability of the oil composition.

TABLE 4

PDSC Oxidation Stability Test Results

| Oil Composition No. | Compound | Oil Formulation (98.5 wt. %) | ZDDP[2] | Oxidation Induction Time (min) |
|---|---|---|---|---|
| 16 | 1 (0.5 wt. %) | B | 1.0 wt. % | 82.6 |
| 23 | 11 (0.5 wt. %) | B | 1.0 wt. % | 115.9 |
| 24 | 10 | B | 1.0 wt. % | 142.4 |
| V | None[1] | B | 1.0 wt. % | 62.2 |
| VII | None[1] | B | None | 15.3 |
| 27 | 11 (0.5 wt. %) | C[3] | 1.0 wt. % | 15.1 |
| VI | None[1] | C[3] | 1.0 wt. % | 10.7 |

[1]0.5 wt % of Solvent Neutral 150 added instead of a compound
[2]Zinc dialkyldithiophosphate
[3]Oil Formulation B without antioxidant The results in Table 4 above demonstrate the unexpected stability imparted to the oil compositions by the addition of the dithiocarbamyl derivatives of this invention, particularly in combination with alkylated diphenylamine (ADPA) antioxidants and ZDDP.

Example D

Cameron-Plint TE77 High Frequency Friction Machine Friction Modifier Test

The oil compositions described in Table 5 below were tested for friction reducing ability.

10 ml of each oil composition was placed in the test chamber of the TE77 so as to cover a flat stationary hardened ground NSOH B01 Gauge Plate (RC 60/0.4 micron). A reciprocating nitrided steel dowel pin (16 mm long, 6 mm diameter, 60 Rc) was then placed on top of the steel plate under 50 Newton load, heated from room temperature to 35° C. over a 10 minute period, and then maintained at 35° C. for an additional 5 minutes. The temperature was then ramped up to 50° C. over 10 minutes and maintained at 50° C. for an additional 5 minutes. Finally, the load was increased to 100 Newtons and the temperature was ramped up to 165° C. over 1 hour. The Friction Coefficient (FC) data was collected between 60–160° C. by measuring frictional force (FF) (FC=FF/load).

The gauge plate was cleaned between runs with hexanes and #500 emery cloth. A new dowel pin or surface of the dowel pin was used for each run.

A reference oil was run alternately between the test oil compositions. The same gauge plate was used until the reference oil no longer provided reproducible results.

TABLE 5

Cameron-Plint TE77 High Frequency Friction Machine
Friction Modifier Test Results

| Oil Composition No. | Oil | | Friction Coefficient | | |
|---|---|---|---|---|---|
| | Compound | Formulation | 60° C. | 110° C. | 160° C. |
| 1 | 1 (1.0 wt. %) | A (99 wt. %) | 0.123 | 0.120 | 0.075 |
| 17 | 5 (0.5 wt. %) | A (99.5 wt. %) | 0.126 | 0.125 | 0.099 |
| 18 | 5 (1.0 wt. %) | A (99 wt. %) | 0.127 | 0.115 | 0.088 |
| I | None[1] | A (99 wt. %) | 0.120 | 0.126 | 0.130 |
| 19 | 7 (0.5 wt. %) | A (99.5 wt. %) | 0.127 | 0.125 | 0.100 |
| 20 | 8 (0.5 wt. %) | A (99.5 wt. %) | 0.0525 | 0.045 | 0.080 |
| 21 | 9 (0.5 wt. %) | A (99.5 wt. %) | 0.118 | 0.075 | 0.055 |
| 22 | 11 (1.0 wt. %) | A (99.0 wt. %) | 0.105 | 0.070 | 0.070 |

[1] 1 wt % of Solvent Neutral 150 added instead of a compound

In Table 5 above, the friction coefficient of the oil compositions decreases with an increase in the friction reducing effectiveness at high engine operating temperatures. In other words, the lower the friction coefficient value the better the additive is at reducing friction.

What is claimed is:

1. A dithiocarbamyl compound of the formula

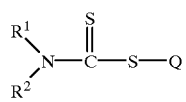

(I)

wherein
Q is a)

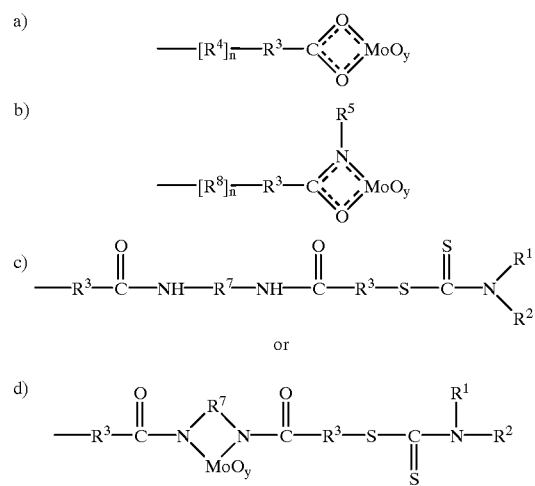

$R^1$ and $R^2$ are each independently $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^3$ is $C_1$–$C_{20}$ alkylene; $R^4$ is —$R^3$—C(O)—O—; $R^5$ and $R^6$ are each independently hydrogen, $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl;

$R^7$ is $C_1$–$C_{20}$ alkylene, optionally substituted with —$OR^5$ or —COOH;

$R^8$ is —$R^3$—C(O)—$NR^5$—; m, n, and y are each, independently, 0, 1, 2 or 3.

2. A dithiocarbamyl compound as recited in claim 1 wherein $R^1$ and $R^2$ are each independently a straight-chained, branched or cyclic alkyl group of from about 2 to about 30 carbon atoms; $R^3$ is a divalent alkylene group of from about 2 to about 12 carbon atoms; $R^5$ and $R^6$ are each independently, hydrogen, a straight-chained, branched or cyclic alkyl group of from about 2 to about 30 carbon atoms; $R^7$ is a divalent alkylene group of from about 2 to about 12 carbon atoms, optionally substituted with —$OR^5$ or —COOH; m is 1; n is 1; and y is 2.

3. A dithiocarbamyl compound as recited in claim 2 wherein $R^1$ and $R^2$ are each independently a straight-chained, branched or cyclic alkyl group of from about 4 to about 24 g carbon atoms; $R^3$ is a divalent alkylene group of from 2 to about 6 carbon atoms; $R^5$ and $R^6$ are hydrogen or an alkyl group of from about 4 to about 24 carbon atoms; and $R^7$ is a divalent alkylene group of from 2 to about 6 carbon atoms substituted with —$OR^5$ or —COOH.

4. A dithiocarbamyl compound as recited in claim 1 which has the formula

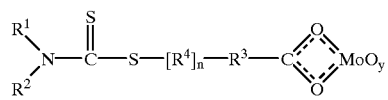

(IA)

wherein $R^1$, $R^2$, $R^3$, $R^4$, n, and y are as defined in claim 1.

5. A dithiocarbamyl compound as recited in claim 1 which has the formula

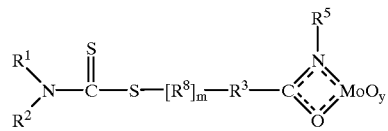

(IB)

wherein $R^1$, $R^2$, $R^3$, $R^8$, m, and y are as defined in claim 1.

6. A dithiocarbamyl compound as recited in claim 1 which has the formula

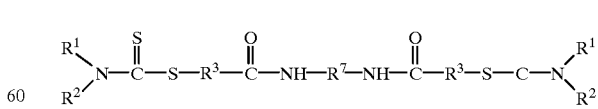

(ID)

wherein $R^1$, $R^2$, $R^3$, and $R^7$ are as defined in claim 1.

7. A dithiocarbamyl compound as recited in claim 1 which has the formula (IE)

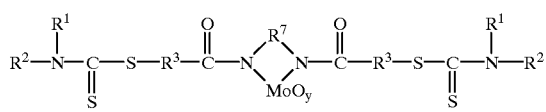

wherein $R^1$, $R^2$, $R^3$, and $R^7$ are as defined in claim 1.

8. A lubricating oil composition comprising a lubricating oil and a functional property-improving amount of at least one dithiocarbamyl compound of claim 1.

9. A lubricating oil composition comprising a lubricating oil and an antiwear-improving amount of at least one dithiocarbamyl compound of claim 1.

10. A lubricating oil composition comprising a lubricating oil and an antioxidant-improving amount of at least one dithiocarbamyl compound of claim 1.

11. A lubricating oil composition comprising a lubricating oil and a friction reducing amount of at least one dithiocarbamyl compound of claim 1.

12. A method for improving at least one functional property of a lubricating oil which comprises adding to the lubricating oil a functional property-improving amount of at least one dithiocarbamyl compound of claim 1.

13. A method for improving the anti-wear property of a lubricating oil which comprises adding to the lubricating oil an anti-wear-improving amount of at least one dithiocarbamyl compound of claim 1.

14. A method for improving the friction reducing property of a lubricating oil which comprises adding to the lubricating oil a friction reducing amount of at least one dithiocarbamyl compound of claim 1.

15. A method for improving the antioxidant property of a lubricating oil which comprises adding to the lubricating oil an antioxidant-improving amount of at least one dithiocarbamyl compound of claim 1.

16. A dithiocarbamyl compound of the formula (IC)

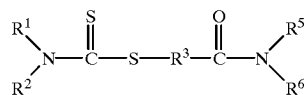

wherein $R^1$ and $R^2$ are each independently $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^3$ is $C_2$–$C_{20}$ alkylene; $R^4$ is —$R^3$—C(O)—O—; $R^5$ and $R^6$ are each independently hydrogen, $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^7$ is $C_1$–$C_{20}$ alkylene, optionally substituted with —$OR^5$ or —COOH; $R^8$ is —$R^3$—C(O)—$NR^5$—; m, n, and y are each, independently, 0, 1, 2 or 3.

17. A dithiocarbamyl compound as recited in claim 16 wherein $R^1$ and $R^2$ are each independently a straight-chained, branched or cyclic alkyl group of from about 2 to about 30 carbon atoms; $R^3$ is a divalent alkylene group of from about 2 to about 12 carbon atoms; $R^5$ and $R^6$ are each independently, hydrogen, a straight-chained, branched or cyclic alkyl group of from about 2 to about 30 carbon atoms; $R^7$ is a divalent alkylene group of from about 2 to about 12 carbon atoms, optionally substituted with —$OR^5$ or —COOH; m is 1; n is 1; and y is 2.

18. A dithiocarbamyl compound as recited in claim 17 wherein $R^1$ and $R^2$ are each independently a straight-chained, branched or cyclic alkyl group of from about 4 to about 24 g carbon atoms; $R^3$ is a divalent alkylene group of from 2 to about 6 carbon atoms; $R^5$ and $R^6$ are hydrogen or an alkyl group of from about 4 to about 24 carbon atoms; and $R^7$ is a divalent alkylene group of from 2 to about 6 carbon atoms substituted with —$OR^5$ or —COOH.

19. A lubricating oil composition comprising a lubricating oil and a functional property-improving amount, an antiwear-improving amount, an antioxidant-improving amount, or a friction reducing amount, of at least one dithiocarbamyl compound of claim 17.

20. A method for improving a lubricating oil which comprises adding to the lubricating oil a functional property-improving amount, an antiwear-improving amount, an antioxidant-improving amount, or a friction reducing amount, of at least one dithiocarbamyl compound of claim 17.

* * * * *